United States Patent [19]

Mengler et al.

[11] 3,998,812
[45] Dec. 21, 1976

[54] NEW STYRYL-PYRAZOLINE COMPOUNDS

[75] Inventors: Helmut Mengler, Frankfurt am Main; Günter Rösch, Altenhain, Taunus; Erich Schinzel, Hofheim, Taunus; Otto Smerz, Kelkheim, Taunus, all of Germany

[73] Assignee: Hoechst Aktiengesellschaft, Frankfurt am Main, Germany

[22] Filed: Mar. 7, 1974

[21] Appl. No.: 449,075

Related U.S. Application Data

[60] Division of Ser. No. 168,768, Aug. 3, 1971, Pat. No. 3,835,126, which is a continuation-in-part of Ser. No. 816,388, April 15, 1969, abandoned.

[30] Foreign Application Priority Data

Apr. 19, 1968 Switzerland .................... 5801/68

[52] U.S. Cl. .............................. 260/239.9; 252/8.6; 252/543; 260/239.6; 260/239.65; 260/240.9; 252/301.22

[51] Int. Cl.² ............ C07D 231/42; C07D 233/00; C07D 235/00; C07D 261/16

[58] Field of Search .................. 260/239.9

[56] References Cited

UNITED STATES PATENTS

| | | | |
|---|---|---|---|
| 2,837,485 | 6/1958 | Siegrist | 252/301.2 |
| 3,133,080 | 5/1964 | Sarkar et al. | 260/310 |
| 3,255,203 | 6/1966 | Shinzel et al. | 260/310 |
| 3,378,389 | 4/1968 | Schellhammer et al. | 117/33.5 |
| 3,498,791 | 3/1970 | Rauhut et al. | 260/239.9 |
| 3,522,242 | 7/1970 | Schinzel et al. | 260/239.9 |
| 3,630,895 | 12/1971 | Krause et al. | 252/8.75 |
| 3,835,126 | 9/1974 | Mengler et al. | 260/239.9 |

*Primary Examiner*—Albert T. Meyers
*Assistant Examiner*—D. W. Robinson
*Attorney, Agent, or Firm*—Curtis, Morris & Safford

[57] ABSTRACT 1,5-Diaryl-3-styryl pyrazolines, which are obtained by condensation of a distyryl ketone and an aliphatic 4-hydrazino-phenyl sulfone, are useful as optical brighteners, especially in admixture with known 1,3-diaryl pyrazoline brighteners.

5 Claims, No Drawings

STYRYL-PYRAZOLINE COMPOUNDS

This is a division of application Ser. No. 168,768 filed Aug. 3, 1971, now U.S. Pat. No. 3,835,126, which in turn is a continuation-in-part of application Ser. No. 816,388 filed Apr. 15, 1969, now abandoned.

The present invention relates to new 1,5-diaryl-3-styryl-$\Delta^2$-pyrazoline compounds and to their use as optical brighteners, in particular in admixture with similar 1,3-diaryl-$\Delta^2$-pyrazolines.

Pyrazoline compounds containing a styryl radical in the 3-position are already known. French Pat. No. 1,095,010, for instance, describes 3-styryl-$\Delta^2$-pyrazolines which carry an aromatic radical in the 1-position and which contain, in addition to alkyl, alkoxy, amino, alkylated and acylated amino groups and halogen atoms, at least one sulfonic acid group as a substituent.

The present invention relates to new styryl pyrazolines of the general formula I

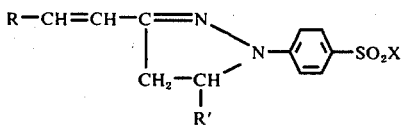

in which R and R' each represent an aryl radical, preferably phenyl and in particular p-chlorophenyl, and X means vinyl or the grouping —$CH_2$—$CH_2$—Y, wherein Y stands for the radical of a compound containing active hydrogen as hereinafter defined. These compounds can be prepared by condensing a dibenzal compound of the general formula II

in which R and R' each have the meanings indicated above, at temperatures in the range of from about 60° to about 130° C with 4-hydrazino-phenyl-$\beta$-hydroxyethyl sulfone, if desired converting the styryl pyrazolines (I, X = —$CH_2$—$CH_2$—OH) thus obtained into their mineral acid esters, preferably the sulfuric acid esters (I, X = —$CH_2$—$CH_2$—O—$SO_3$Me, Me = a hydrogen atom or a cation), if desired transforming these acid esters, by treatment with agents having an alkaline action, into the vinyl sulfone compounds (I, X = —CH=$CH_2$) and adding to these compounds, optionally in the presence of alkaline catalysts, compounds of the formula H—Y containing active hydrogen as hereinafter defined.

As compounds containing active hydrogen there are understood compounds of the formula H—Y, in which Y may also carry further active hydrogen atoms, wherein Y is halogen, hydroxy, sulfato, sulfo or one of the following groups:

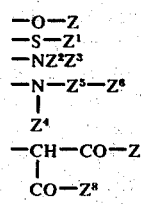

in which Z is alkyl of 1 to 18 carbon atoms, cyclohexyl, benzyl; lower alkyl substituted by hydroxy, lower alkoxy, di(lower alkyl) amino, morpholyl, piperidyl or piperazyl or the lower alkyl sulfate, lower alkyl-(phenyl sulfonate) or tosylate or lower alkyl halide quaternary salts of said nitrogen containing substituents;

$Z^1$ is lower alkyl, benzyl, phenyl or lower alkyl substituted by carboxy or lower carboalkoxy;

$Z^2$ is alkyl of 1 to 18 carbon atoms, cyclohexyl, benzyl or lower alkyl substituted by hydroxy, carboxy, sulfo, lower carboalkoxy, amino or mono- or di-(lower alkyl)-amino;

$Z^3$ is hydrogen, lower alkyl or lower hydroxyalkyl;

$Z^2$ and $Z^3$ together with the nitrogen are morpholine, piperidine or piperazine;

$Z^4$ is hydrogen, alkyl of 1 to 18 carbon atoms, or benzyl;

$Z^5$ is —CO— or —$SO_2$—;

$Z^6$ is hydrogen, alkyl of 1 to 18 carbon atoms, cyclohexyl, benzyl, phenyl, chlorophenyl, lower-alkyl-phenyl, lower alkoxy-phenyl, amino or lower alkoxy, or $Z^4$ and $Z^6$ together are $(CH_2)_x$ wherein x is an integer of 2 to 5 or, if $Z^5$ is CO, $Z^6$ and $Z^4$ together are —NH—$CH_2$—$CH_2$—, in which bridge-member the nitrogen is bound to —CO—; and $Z^7$ and $Z^8$ are methyl or lower alkoxy.

For the esterification of the $\beta$-hydroxyethyl sulfone compound (I, X = —$CH_2$—$CH_2$—OH) there are used, for example, hydrohalic acids such as hydrochloric acid, but preferably sulfuric acid.

The alcohols which enter into consideration are primary and secondary alkanols containing 1 to 18 carbon atoms, which may carry as substituents e.g. hydroxy or lower alkoxy groups, but preferably di-(lower-alkyl)-amino and tri-(lower alkyl)-ammonium groups, for example methanol, ethanol, n-propanol, i-propanol, n-butanol, dodecyl alcohol, stearyl alcohol, butanediol-1,3,methylglycol, dimethylaminoethanol, diethylaminoethanol, di-n-butylaminoethanol, 1-dimethylaminopropanol-2, N-$\beta$-hydroxyethylpiperidine; further cyclohexanol and benzyl alcohol. Analogously, mercaptans, for example ethyl or benzyl mercaptan may be added to the vinyl group.

As amines there may be used primary and secondary alkyl amines of 1 to 18 carbon atoms in the alkyl chains, which may carry as substituents, for example, carboxylic acid and sulfonic acid groups, hydroxy, amino and, preferably, dialkyl amino groups. There are mentioned, for example: methyl amine, ethylamine, n-propylamine, n-butylamine, stearylamine, ethanolamine, cyclohexylamine, benzylamine, dimethylamine, diethylamine, di-n-butylamine, diethanolamine, N-methyltaurine, N-methylglycine, $\beta$-diethyl-aminoethylamine, N-methyl-benzylamine, piperidine, morpholine, ethylenediamine, piperazine, $\beta$-dimethylamino-ethylamine or $\gamma$-diethylamino-n-propylamine.

As acid amides, the amide nitrogen of which still carries at least one hydrogen atom, there may be used carboxylic acid amides, lactams, amides of carbonic acid such as ureas and urethanes, as well as their thio derivatives, moreover sulfonic acid amides. There may be mentioned, by way of example: formamide, acetamide, propionic acid amide, n-butyric acid amide, n-valeric acid amide, caproic acid amide, diethyl-acetic acid amide, hexahydrobenzamide, benzamide, 4-methyl-benzamide, 4-methoxy-benzamide, N-methyl acetamide, N-ethyl acetamide, N-n-propyl-acetamide, N-stearyl-acetamide, N-methyl-benzamide, acetanilide, N-benzyl acetamide and benzanilide. Furthermore urea, imidazolidinone-(2), ethyl urethane, azetidinone-(2), ε-caprolactam as well as benzene sulfonic acid amide and p-toluene sulfonic acid amide may be used.

The C—H—acidic compounds may be, for example, malonic esters, acetoacetic acid esters and acetyl acetone.

As dibenzal compounds of the formula II

(which may be obtained, for example, by condensation of 1 mole of acetone with 2 moles of an aromatic aldehyde, for example, benzaldehyde, p-tolylaldehyde, o-, m- and p-chlorobenzaldehyde, 3,4-dichlorobenzaldehyde, p-fluoro-benzaldehyde, p-cyanobenzaldehyde, p-carboxybenzaldehyde, p-methoxybenzaldehyde, p-carbomethoxybenzaldehyde or p-trifluoromethylbenzaldehyde,) there are preferably used the easier accessible symmetrical products.

For the condensation of the dibenzal compounds of formula II with 4-hydrazino-phenyl-β-hydroxy-ethyl sulfone, approximately equimolar amounts thereof are boiled for several hours in ethanol. By the addition of a minor amount of concentrated hydrochloric acid, the reaction is substantially accelerated and the yields are distinctly increased.

The esterification of the hydroxy ethyl sulfone compounds (formula I, $X = -CH_2-CH_2-OH$) with concentrated sulfuric acid is carried out under cooling, preferably at temperatures in the range of from about 0 to about 10° C. If the temperature is allowed to rise above this value, water-soluble products are formed, which are different from the desired sulfuric acid ester and cannot be transformed, like this ester, into the vinyl sulfone compound. It is suitable to separate the sulfuric acid esters, (formula I, $X = -CH_2-CH_2-O-SO_3Me$) in the form of the potassium salts (Me = K), since these salts crystallize better than e.g. the corresponding sodium compounds.

The quantity of alkali used for the conversion of the sulfuric acid esters into the vinyl compounds (formula I, $X = -CH=CH_2$) — for economic reasons it is suitable to use sodium hydroxide solution - must be sufficient for adjusting and maintaining a pH-value of about 10 to about 11. If, while stirring at a raised temperature (about 50° to 70° C ), the pH-valve decreases, further amounts of alkali must be added in order to maintain the pH-value constant. In some cases it is of advantage to operate in the presence of acetone; this solvent accelerates the crystallization of difficultly crystallizable vinyl sulfone compounds.

The addition of primary and secondary amines to the vinyl sulfone compounds (formula I, $X = -CH=CH_2$) is suitably carried out with an excess amount of the amine in the presence of an organic, preferably water-miscible, solvent, such as dioxane, dimethylformamide or ethanol. Mixtures of water and the said solvents may also be used. The reaction temperature is adjusted to a temperature between about 40° and about 100° C, preferably to a temperature in the range of from about 60° to about 80° C. The simultaneous use of alkaline catalysts is not necessary.

For the addition of acid amides, having at least one hydrogen atom at the nitrogen to the vinyl-sulfone compounds (formula I, $X = -CH=CH_2$), mixtures of the components containing the amide in excess may be heated in the presence of catalytic amounts of alkali, preferably in the presence of sodium methylate, for a short time to temperatures in the range from 100° to 200° C, preferably from about 115° to about 140° C. This reaction, too, is suitably carried out in the presence of an inert organic solvent such as toluene or chlorobenzene. If solvents are used, the reaction temperature may be lowered to about 50° to 80° C, but the reaction time may then be several hours.

For the addition of alcohols, phenols and their thioderivatives, which may carry further substituents, the vinyl-sulfone compounds (formula I, $X = -CH=CH_2$) are reacted in an excess of the corresponding hydrogen-active compound and, after the addition of a catalytic amount of alkali, for example in the presence of sodium methylate or concentrated sodium hydroxide solution, at temperatures ranging from about 40° to about 80° C.

The addition products of alcohols substituted by basic groups such as dimethylamino-ethanol, diethylamino-ethanol, di-n-butylamino-ethanol or 1-dimethylamino-propanol-2, may be further converted in known manner, by the action of alkylating agents such as alkyl halides, dimethyl sulfates, diethyl sulfates, benzyl halides, benzene or p-toluene sulfonic acid lower alkyl esters, especially methyl esters, into the corresponding quarternary ammonium compounds.

The addition of salts of sulfurous acid may be effected by heating the vinyl sulfone compounds (formula I, $X = -CH=CH_2$) in a mixture of water and dioxane to about 90° to 100° C in the presence of sodium sulfite, and maintaining the pH-value constant, during the reaction, at 9.5 by dropwise addition of dilute mineral acid.

The compounds obtainable according to the invention have, in crystalline form, a yellow color and, in solution, show a strong blue to greenish-blue fluorescence. They are suitable for the optical brightening of colorless substrates, for example textiles, in particular in admixture with pyrazoline compounds that have a violet-blue fluorescence and correspond to the following general formula III

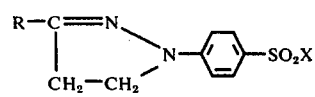

in which R and X have the meanings indicated above. Suitable pyrazoline compounds of the formula III are disclosed, for example, in Belgian Pat. Nos. 631,267, 661,139, 670,161 and 701,986.

Especially good brightening effects are obtained when the compounds of formulas I and III have the same radical X and if the compounds of the formula I are contained in the mixtures in an amount of about 0.05 to about 10%, preferably about 0.5 to about 3%.

These mixtures have a brightening action which is, with regard to the brilliancy of the degree of whiteness, distinctly superior to that of the individual components. This unexpected synergistic effect can be observed especially with textile materials of polyamides, cellulose esters and polyacrylonitrile. The said mixtures may also be used, with good result, for the brightening of mixed textiles which may consist of the said fibrous materials and other synthetic or natural fibres.

The said mixtures are clearly superior to the individual components also with regard to the various application methods. This is true in the case of exhaust processes in the usual temperature range of about 30° to about 140° C, for paddingsteaming or for thermosol processes (padding followed by a dry heat treatment). In these cases, the textile material is impregnated with a bath containing the brightening dispersion, squeezed to a moisture content of about 20 to about 150%, and subsequently steamed at about 100° to 150° C or subjected to a heat treatment in the range of about 140° to 210° C. The thermosol treatment may also be combined with the steaming process.

The fastnesses to light of the said brightening mixtures correspond to those of the individual components.

Because of the variability of the radical X, the compounds of the invention permit adaptation of the affinity of the brighteners to fibrous materials of different kind. This applies especially to the above-mentioned mixtures of compounds of the formulas I and III, which are identical in the radical X. In this respect, the new compounds are far superior to the pyrazolines known from French Pat. No. 1,095,010.

The following Examples serve to illustrate the invention, but they are not intended to limit it thereto. All parts and percentages are by weight unless otherwise stated, the ratio of parts by weight to parts by volume being the same as that of the kilogram to the liter.

EXAMPLE 1

23.4 Parts by weight of dibenzal acetone and 21.6 parts by weight of 4-hydrazino-phenyl-$\beta$-hydroxyethyl sulfone were boiled under reflux for 4 hours, while stirring, in 400 parts by volume of alcohol to which 10 parts by volume of concentrated hydrochloric acid had been added. The mixture was cooled and stirred for further 2 hours while cooling with ice. The precipitated reaction product was suction-filtered and, after having been washed several times with alcohol, dried under reduced pressure at 60° C. 39 Parts by weight of the condensation product (90% of the theoretical yield) were obtained. After repeated dissolution and recrystallization from alcohol, the 1-[4'-($\beta$-hydroxyethyl-sulfonyl)phenyl]-3-Styryl-5-phenyl-$\Delta^2$-pyrazoline IV (Table 1) showed a melting point of 171° to 172° C.

When using 30.3 parts by weight of 4,4'-dichloro-dibenzal-acetone, 45 parts by weight (90% of the theoretical yield) of 1-[4'-($\beta$-hydroxy-ethyl-sulfonyl)-phenyl]-3-p-chlorostyryl-5-p-chloro-phenyl-$\Delta^2$-pyrazoline XVI (Table 2) were obtained which, after repeated dissolution and recrystallization from alcohol and butanol, had a melting point of 201° to 203° C.

EXAMPLE 2

108 Parts by weight of the compound IV (Example 1) were introduced, while stirring and cooling with ice, into 300 parts by volume of concentrated sulfuric acid and stirred for about further 20 hours at a temperature below +10° C. The solution so-obtained was allowed to run into a mixture of 405 parts by weight of potassium chloride and 1100 parts by volume of water, the temperature being kept below +10° C by the addition of 1100 parts by weight of ice. The mixture was stirred for two hours. The pricipitated potassium salt of the sulfuric acid ester was suction-filtered and washed with a 20% aqueous potassium chloride solution until the washings were neutral.

The moist potassium salt of the sulfuric acid ester of the hydroxy ethyl sulfone compound IV was introduced into a mixture of 3000 parts by volume of water and 500 parts by volume of acetone, and heated to the boil while stirring. At this temperature, 150 parts by volume of 2N sodium hydroxide solution were added in one portion. The mixture was allowed to cool, while stirring, for 1½ hour. The precipitated compound was filtered with suction at 50° C and washed with water until the washings were neutral. After drying at 60° C under reduced pressure, 86 parts by weight (83% of the theoretical amount) of the vinyl compound were obtained. After repeated dissolution and recrystallization from butanol, the 1-[4'-(vinylsulfonyl)-phenyl]-3-styryl-5-phenyl-$\Delta^2$-pyrazoline V (Table 1) had a melting point of 180° to 182° C.

When 125 parts by weight of the compound XVI were used, the potassium salt of the sulfuric acid ester was obtained in the same manner.

The moist potassium salt of the sulfuric acid ester of the hydroxy ethyl sulfone compound XVI was introduced into 4000 parts by volume of water and heated, while stirring, to 70° – 75° C. At this temperature, 150 parts by volume of 2N sodium hydroxide solution were added in one portion. The mixture was stirred for further 2 hours at 70° C, filtered hot with suction and washed until the washings were neutral. After drying at 60° C under reduced pressure, 118 parts by weight of 1-[4'-(vinylsulfonyl)-phenyl]-3-p-chlorostyryl-5-p-chlorophenyl-$\Delta^2$-pyrazoline XVII (Table 2) were obtained, which corresponded to a yield of 96% of the theoretical amount. After repeated dissolution and recrystallization from butanol, the compound melted at 170° to 172° C.

EXAMPLE 3

41.4 Parts by weight of the vinyl sulfone compound V were introduced into a solution of 40 parts by weight of sodium sulfite in 400 parts by volume of water and 100 parts by volume dioxan. The mixture was heated to 90° to 95° C while stirring, the pH-value of the solution being maintained constant at 9.3 to 9.8 by dropwise addition of 2N hydrochloric acid, for which an amount of about 50 parts by volume of 2N hydrochloric acid was required. When the reaction mixture did not change its pH-value, the mixture was diluted with 400 parts by volume of water and the solution formed was filtered at 95° C after the addition of kieselguhr. 100 Parts by weight of sodium chloride were added to the filtrate, which was allowed to cool, while stirring. The precipitated sodium salt of 1-[4'-($\beta$-sulfo-ethyl-sulfonyl)-phenyl]-3-styryl-5-phenyl-$\Delta^2$-pyrazoline VI (Table 1) was suction-filtered, washed with 1000 parts by volume of a 10% sodium chloride solution and dried at 60° C under reduced pressure. The yield amounted to 54 parts by weight of a compound of 95% strength (content of NaCl 5%), which corresponded to 99% of the theoretical yield.

When 48.3 parts by weight of the vinyl sulfone compound XVII were used, the process was carried out in the presence of 200 parts by volume of dioxan. When the reaction was completed, the mixture was diluted with 1000 parts by volume of water. After filtration the product was not salted out with sodium chloride. The sodium salt, precipitated in the cold, of 1-[4'-($\beta$-sulfo-ethyl-sulfonyl)-phenyl]-3-p-chlorostyryl-5-p-chlorophenyl-$\Delta^2$-pyrazoline XVIII (Table 2) was filtered with suction, washed with 1000 parts by volume of a 5% sodium chloride solution and dried at 60° C under reduced pressure. 54 Parts by weight of a compound of 99% strength (content of NaCl 1%), i.e. 96% of the theoretical yield, were obtained.

EXAMPLE 4

41.4 Parts by weight of the vinyl sulfone compound V were introduced into 100 parts by weight of 1-dimethylaminopropanol-(2). 2.5 Parts by weight of a 33% sodium hydroxide solution were added while stirring and the reaction mixture was heated for 1 hour at 60° C. Subsequently, 80 parts by weight of isopropanol were added, the mixture was cooled until it reached a temperature of +5° C and stirred for another hour in an ice bath. The precipitated reaction product was filtered with suction, washed first with 50 parts by volume of isopropanol and then with water. After drying, 41 parts by weight of the addition product (79% of the theoretical yield) were obtained. The addition product VII (Table 1) of 1-dimethyl amino-propanol-(2) and the vinyl compound V melted at 100° to 102° C, after having been several times dissolved and recrystallized from isopropanol.

When 48.3 parts by weight of the vinyl sulfone compound XVII were used, 52 parts by weight (89% of the theoretical yield) of the addition product XIX (Table 2) with a melting point of 134° to 136° C (from butanol) were obtained.

EXAMPLE 5

50 Parts by weight of the vinyl sulfone compound V were introduced in a stirred mixture of 200 parts by volume of chlorobenzene and 13 parts by weight of acetamide. 1 Part by weight of sodium methylate was added to the batch, which was heated to an internal temperature of 80° C. The mixture was stirred for a further 2½ hours at this temperature, subsequently cooled to 15° C and kept at this temperature for 1 hour. The precipitated reaction product was then filtered with suction, washed with 40 parts by volume of chlorobenzene, and subsequently washed with methanol and water. The 1-[4'-($\beta$-acetylamino-ethyl)-sulfonyl)-phenyl]-3-styryl-5-phenyl-$\Delta^2$-pyrazoline VIII (Table 1) dried under reduced pressure at 60° C (41 parts by weight, 73% of the theoretical yield) melted, after several dissolutions and recrystallizations from toluene, at 184 to 187° C.

When 58 parts by weight of the vinyl sulfonic compound XVII were used, 47.5 parts by weight (88% of the theoretical yield) of 1-[4'-($\beta$-acetylamino-ethylsulfonyl)-phenyl]-3-p-chlorostyryl-5-p-chlorophenyl-$\Delta^2$-pyrazoline XX (Table 2) were obtained, which melted after several dissolutions and recrystallizations from benzene at 117° to 119° C.

EXAMPLE 6

8.3 Parts by weight of the vinyl sulfone compound V were introduced into a stirred mixture of 50 parts by volume of ethanol and 3 parts by weight of n-butyl amine. The mixture was heated to the boil, kept at boiling temperature for about 1 hour and cooled. The reaction product formed was stirred for another hour in an ice bath and thus allowed to crystallize completely. The product was suction-filtered, washed with ethanol and dried at 60° C under reduced pressure. 8.7 Parts by weight (89% of the theoretical yield) of the addition product were obtained. The 1-[4'-($\beta$-butylamino-ethylsulfonyl)-phenyl]-3-styryl-5-phenyl-$\Delta^2$-pyrazoline IX (Table 1) had a melting point of 135° to 135° C after several dissolutions and recrystallizations from ethanol.

EXAMPLE 7

8.3 Parts by weight of the vinyl sulfone compound V were introduced into a stirred mixture of 50 parts by volume of n-butanol and 2 parts by volume of a 33% sodium hydroxide solution, and heated to 60° C. After heating for 1 hour at this temperature, the reaction product was cooled until a temperature of 35° C had been attained, filtered with suction, washed with butanol and methanol and subsequently with water until the washings were neutral. After drying at 60° C under reduced pressure, 9 parts by weight (92% of the theoretical yield) of the adduct were obtained. After purification from butanol, the 1-[4'-($\beta$-butoxy-ethyl-sulfonyl)-phenyl]-3-styryl5-phenyl-$\Delta^2$-pyrazoline XI (Table 1) melted at 126 to 127° C.

EXAMPLE 8

51.7 Parts by volume of the compound VII were introduced into 400 parts by volume of water and stirred for 1 hour at room temperature after the addition of 13 parts by weight of dimethyl sulfate. A clear yellowish solution was obtained, which was stirred for further 2 hours at room temperature after the addition of 5 parts by weight of 1-dimethylaminopropanol. The solution which had thus been freed from excess dimethyl sulfate was neutralized with dilute hydrochloric acid and diluted with water to a weight of 517 parts. Thus a solution containing 10%, referred to the weight of the free base, was obtained.

Table 1

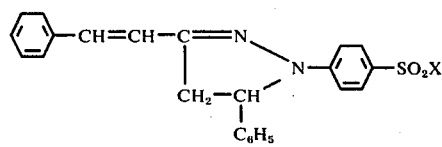

| No. | X = | Melting point ° C |
|---|---|---|
| IV | —CH$_2$CH$_2$OH | 171 – 172 |
| V | —CH=CH$_2$ | 180 – 182 |
| VI | —CH$_2$CH$_2$SO$_3$Na | — |
| VII | —CH$_2$CH$_2$O—CH(CH$_3$)—CH$_2$N(CH$_3$)$_2$ | 100 – 102 |
| VIII | —CH$_2$CH$_2$NHCOCH$_3$ | 184 – 187 |
| IX | —CH$_2$CH$_2$NHC$_4$H$_9$(n) | 135 – 136 |
| X | —CH$_2$CH$_2$N(C$_2$H$_5$)$_2$ | 146 – 147 |
| XI | —CH$_2$CH$_2$OC$_4$H$_9$(n) | 126 – 127 |
| XII | —CH$_2$CH$_2$OCH(CH$_3$)$_2$ | 143 – 144 |
| XIII | —CH$_2$CH$_2$OCH$_2$CH$_2$N(CH$_3$)$_2$ | 119 – 121 |

Table 1-continued

Structure: Ph-CH=CH-C(=N-N(-CH₂-CH(C₆H₅)-)- )-C₆H₄-SO₂X

| No. | X= | Melting point °C |
|---|---|---|
| XIV | $-CH_2CH_2O-CH(CH_3)-CH_2-\overset{(+)}{N}(CH_3)_3]^+ \; CH_3OSO_3^-$ | — |
| XV | $-CH_2CH_2NHCH_2CH_2N(C_2H_5)_2$ | 72 – 73 |

Table 2

Structure: Cl-C₆H₄-CH=CH-C(=N-N(-CH₂-CH(C₆H₄Cl(p))-)-)-C₆H₄-SO₂X

| No. | X = | Melting point °C |
|---|---|---|
| XVI | $-CH_2CH_2OH$ | 201 – 203 |
| XVII | $-CH=CH_2$ | 170 – 172 |
| XVIII | $-CH_2CH_2SO_3Na$ | — |
| XIX | $-CH_2CH_2O-CH(CH_3)-CH_2N(CH_3)_2$ | 134 – 136 |
| XX | $-CH_2CH_2NHCOCH_3$ | 117 – 119 |
| XXI | $-CH_2CH_2NHC_{12}H_{25}$ | 104 – 107 |
| XXII | $-CH_2CH_2N(CH_3)_2$ | 176 – 178 |
| XXIII | $-CH_2CH_2OCH_2CH_2OCH_3$ | 140 – 141 |
| XXIV | $-CH_2CH_2OCH_3$ | 165 – 166 |
| XXV | $-CH_2CH_2OCH_2CH_2N(C_4H_9)_2$ | 92 – 94 |
| XXVI | $-CH_2CH_2O-CH(CH_3)-CH_2\overset{(+)}{N}(CH_3)_3]^+ \; CH_3OSO_3^-$ | — |
| XXVII | $-CH_2CH_2NH-CH_2CH_2CH_2N(C_4H_9)_2$ | 97 – 98 |

EXAMPLE 9:

A fabric consisting of polyamide-6 was treated in a bath at a goods-to-liquor ratio of 1:20. The bath contained 0.3 g/l of a mixture of 99.5 parts of a compound of the formula XXVIII

XXVIII

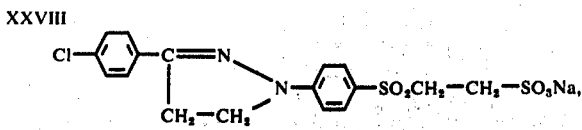

Cl-C₆H₄-C(=N-N(-CH₂-CH₂-)-)-C₆H₄-SO₂CH₂-CH₂-SO₃Na, known from Belgian Pat. No. 631 367, and 0.5 part of the compound of the formula VI. The fabric was treated with this solution for 30 minutes at 80° C. After rinsing with water and drying at 120° C, the fabric had an outstanding degree of whiteness superior to that obtained under the same conditions with the individual components of the said mixture.

EXAMPLE 10

A fabric consisting of polyamide-6,6 was treated in a liquor (goods-to-liquor-ratio 1:10), which contained 0.6 g/l of a mixture of 98 parts of the compound XXVIII of Example 9 and 2 parts of compound VI.

The fabric was treated for 30 minutes at 120° C. After rinsing and drying, it had a very high degree of whiteness, which was clearly superior to that obtained under the same conditions with the individual components of the mixture.

EXAMPLE 11

A fabric consisting of polyamide-6,6 was impregnated with a solution which contained 2.4 g/l of a mixture of 98.5 parts of the compound of the formula XXVIII of Example 9 and 1.5 part of the compound VI.

The textile material thus impregnated was squeezed between rollers to an increase of weight of 100%, and was subsequently subjected, for 30 seconds, to a hot-air treatment at 200° C.

The material thus thermosoled was then printed with suitable dyestuffs and steamed for 20 minutes with saturated steam at 104° C. After rinsing and drying, the fabric treated in this manner had an outstanding degree of whiteness at the unprinted spots, which was better than that obtained, under otherwise analogous conditions, with solutions each containing 2.4 g/l of the individual components of the mixture indicated.

EXAMPLE 12

A yarn consisting of fibers of a mixed polymer of polyacrylonitrile, containing at least 85% of polyacrylonitrile was treated in a liquor (goods-to-liquor ratio 1:40) which contained 0.005 g/l of a mixture of 97 parts of the compound of the formula XXIX $$Cl-\phenyl-\underset{\underset{CH_2-CH_2}{|}}{C}=N\diagdown N-\phenyl-SO_2-CH_2-CH_2OCH\underset{\underset{CH_3}{|}}{}-CH_2N(CH_3)_2,$$
XXIX known from Belgian Pat. No. 670 161, and 3 parts of the compound of formula XIX. The yarn was treated for 30 minutes at boiling temperature. After rinsing and drying, it had a very high degree of whiteness clearly superior to that obtained, under otherwise analogous conditions, by treatment with the individual components of the mixtures indicated and was distinguished by a bluish tint.

EXAMPLE 13:

A fabric consisting of cellulose triacetate was treated in a liquor (goods-to-liquor ratio 1:5) with an aqueous dispersion which contained 4 g/l of a mixture of 96 parts of the compound of the formula XXX $$Cl-\phenyl-\underset{\underset{CH_2-CH_2}{|}}{C}=N\diagdown N-\phenyl-SO_2CH_2CH_2NHCOCH_3,$$
XXX known from Belgian Pat. No. 701 986, and 4 parts of the compound of the formula XX. The fabric was treated for 30 minutes with this liquor at a temperature of 80° C. After rinsing and drying it had an outstanding degree of whiteness by far superior to that obtained, under otherwise the same conditions, with the individual components of the mixture indicated.

EXAMPLE 14

Fabrics of polyamide 6 (polycaprolactame) fibers were brightened following two different processes with the compound of the formula XXVIII (cf. Example 9) alone or together with fluorescent agents in order to compensate the reddish tint of the brightened material obtained when using compound XXVIII alone. The fluorescent agents were:

the compound of the formula XVIII and
the compound of the formula XXXI $$\phenyl-CH=CH-\underset{\underset{CH_2-CH}{|}\phenyl}{C}=N\diagdown N-\phenyl$$

(U.S. Patent No. 2,387,485)

(U.S. Patent No. 2,387,485)

All of the compounds XXVIII, XVIII and XXXI (known from U.S. Pat. No. 2,387,485) were predissolved before use as follows:

100 mg each of the compounds were dissolved in 5 cc of dimethyl formamide with gentle heating and dispersed in 100 cc of distilled water with the aid of a dispersant (being a nonylphenol polyglycolether containing on an average 23 mols of ethylene oxide per each mol of nonylphenol and having a strength of 87%).

1. Exhaustive Process:

Samples of the fabrics were agitated for 30 minutes at 80° C in an aqueous bath containing, referred to the weight of the dry fabric, 0.8% of compound XXVIII. The pH value was adjusted to 4 by means of oxalic acid. Two separate baths contained, furthermore, 0.003% each of compounds XVIII or XXXI. Subsequently, the brightened samples were rinsed and dried in usual manner.

The degree of whiteness of the so-obtained fabrics was determined with the ZEISS-ELREPHO apparatus using the FM filters and standard light C, against the remission of magnesium oxide as a standard defined as having 100% remission. From the so-obtained values the degree of whiteness was calculated according to the formula of Berger (Die Farbe 8 (1959) 187 – 202)

| Brightener | additive | W | tint |
|---|---|---|---|
| — | — | 64.1 | (yellowish) |
| XXVIII | — | 163.1 | reddish-white |
| XXVIII | XVIII | 160.5 | pure white |
| XXVIII | XXXI | 136.9 | greenish white |

2. Pad-Thermosol Process:

Polyamide-6 fabrics were padded with an aqueous liquor containing per liter
   12 g of a dispersion of compound XXVIII in dipropylene glycol of 16% strength
   12 g of an auxiliary mixture consisting of
      85% of polyethyleneglycol (molecular weight 400)
      10% of iso-tridecyl-alcohol oxethylate (containing on an average 51 mols of ethylene oxide)
      2.5% of triisobutylphosphate of 50% strength and
      2.5% of (2-ethylhexyl)-2-ethylcaproate
   1.2 g of an auxiliary consisting of
      55% of disodiumpyrophosphate and
      45% of citric acid.
Two separate batches contained, furthermore, per liter 0.04 g of compound XVIII or XXXI.

The padded fabrics were squeezed between rollers in such a way the squeezed fabric showed an increase of weight of 60%, referred to dry fabric and submitted to a heat treatment at 180° C for 30 seconds. The degree of whiteness was determined as stated above.

Results:

| Brightener | additive | W | tint |
|---|---|---|---|
| XXVIII | — | 145.1 | reddish-white |
| XXVIII | XVIII | 145.5 | pure white |
| XXVIII | XXXI | 136.8 | greenish-white |

3. Exhaustive Process with varying amounts of compound XXXI

In order to verify that compound XXXI is inferior to compound XVIII tests were made with diminishing amounts of compound XXXI. These tests demonstrate that the use of lower amounts of "dyestuff XXXI" causes less decrease of the degree of whiteness since the dyeing power is weakened, but the tint of the brightened fabric is not improved.

The brightening procedure was the same as stated above (item 1). The goods-to-liquor ratio was 1:20. Results:

Results:

| Brightener | additive per liter | | W | tint |
| --- | --- | --- | --- | --- |
| — | — | | 64.1 | (yellowish) |
| XXVIII | — | | 163.1 | reddish-white |
| XXVIII | 0.003g | XVIII | 160.5 | pure white |
| XXVIII | 0.003g | XXXI | 136.9 | greenish white |
| XXVIII | 0.0012g | XXXI | 138.3 | greenish white |
| XXVIII | 0.0009g | XXXI | 140.1 | greenish white |
| XXVIII | 0.0006g | XXXI | 143.0 | greenish white |
| XXVIII | 0.0003g | XXXI | 146.0 | greenish white |

4. Comparison of the Fastness to Weathering

Fabrics were treated in an exhaustive process as described above (item 1) in a bath containing 0.03% of compound XVIII or XXXI, respectively. The so-obtained samples were submitted to the Determination of the Fastness to Weathering according to DIN 54 071 (German Industrial Standard, equivalent to ISO-TC 38-SC[1]) N 310 — Colour Fastness to Weathering: Xenon Lamp) by exposing the wet samples 2 hours to the light of a Xenon burner. During this time the sample rotates and is periodically sprayed with water. A part of the samples is covered. The samples were, subsequently, exposed to the light of a UV lamp. The samples treated with compound XVIII were nearly unchanged in their fluorescence while the sample treated with compound XXXI showed only a very weak fluorescence.

EXAMPLE 15:

Fabrics of polyamide-6,6 fibers were treated for 30 minutes at 80° C in baths containing 0.8%, referred to the weight of the good, of compound XXVIII (Example 9), 1% by weight of oxalic acid and the following amounts of additive:

| Sample | additive | |
| --- | --- | --- |
| 1 | — | |
| 2 | 0.0015 % | XVIII |
| 3 | 0.0022 % | XXXII (equimolar amounts) |

XXXII:

Cl—⟨phenyl⟩—CH=CH—C=N, H₂C—CH, N—⟨phenyl⟩—SO₃Na, with p-Cl-phenyl substituent (known from French Patents Nos. 1,093,063 and 1,095,010).

After rinsing and drying the fabrics showed the following degrees of whiteness (according to the Berger method) W:

| Sample | W | Tint |
| --- | --- | --- |
| 1 | 168.0 | reddish-white |

-continued

| Sample | W | Tint |
| --- | --- | --- |
| 2 | 169.7 | pure white |
| 3 | 163.7 | yellowish white |
| untreated | 85.2 | yellowish white |

EXAMPLE 16

Fabrics made of polyacrylonitrile fibers were treated for 30 minutes at a goods-to-liquor ratio of 1:20, in a boiling bath containing 0.2% of compound XXIX (Example 12), and 1% of oxalic acid. An equivalent bath contained, furthermore, 0.0015% of compound XIX. After rinsing and drying the degree of whiteness was determined according to the Berger method:

| Brightener | degree of whiteness | tint |
| --- | --- | --- |
| none | 65.4 | yellowish |
| XXIX | 152.9 | reddish-white |
| XIX + XXIX | 153.5 | pure white |

EXAMPLE 17

A fabric consisting of cellulose acetate (containing on an average 2.5 mols of aceto groups per glucose unit) was treated at 80° C for 45 minutes in a bath containing 0.3% of compound XXX (Example 13) at a goods-to-liquor ratio of 1:20. An equivalent bath contained, furthermore, 0.002% of compound XX. After rinsing and drying the degree of whiteness was determined by the Berger method:

| Brightener | degree of whiteness | tint |
| --- | --- | --- |
| none | 63.6 | yellowish |
| XXX | 143.8 | reddish-white |
| XX + XXX | 149.8 | pure white |

We claim:
1. A compound of the formula

$$R-CH=CH-C=N \diagdown \atop H_2C-C-H \diagup N-\langle phenyl \rangle -SO_2-CH_2CH_2OZ, \atop R'$$

wherein R and R' are phenyl or phenyl substituted by chlorine and Z is alkyl of 1 to 18 carbon atoms or lower alkyl substituted by lower alkoxy or by di-(lower alkyl)-amino.

2. The compound as claimed in claim 1, wherein R and R' are identical.

3. The compound as claimed in claim 1, wherein R and R' are chlorophenyl.

4. The compound as claimed in claim 1, wherein Z is lower alkyl substituted by di-(lower alkyl amino).

5. The compound as claimed in claim 1, wherein R and R' are p-chlorophenyl and Z is $$-CH-CH_2-N-CH_3. \atop CH_3 \phantom{xxxx} CH_3$$

* * * * *